US 8,568,373 B2

(12) United States Patent
Kuniyasu et al.

(10) Patent No.: US 8,568,373 B2
(45) Date of Patent: Oct. 29, 2013

(54) MEDICAL ELONGATE MEMBER HOUSING TOOL AND MEDICAL ELONGATE MEMBER HOUSING TOOL ASSEMBLY

(75) Inventors: Junko Kuniyasu, Fuji (JP); Junichi Kobayashi, Fujinomiya (JP); Yasushi Kinoshita, Fujinomiya (JP); Tadashi Kousai, Glasgow (GB)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 69 days.

(21) Appl. No.: 13/194,533

(22) Filed: Jul. 29, 2011

(65) Prior Publication Data

US 2012/0022470 A1    Jan. 26, 2012

Related U.S. Application Data

(63) Continuation of application No. PCT/JP2010/050775, filed on Jan. 22, 2010.

(30) Foreign Application Priority Data

Feb. 3, 2009  (JP) ................................. 2009-023098

(51) Int. Cl.
*A61B 17/06*  (2006.01)
(52) U.S. Cl.
USPC ........... 604/265; 206/303; 206/363; 206/364; 206/438; 604/164.02; 604/264; 604/510
(58) Field of Classification Search
USPC ............. 604/164.02, 264, 265, 510; 206/438, 206/63.3, 303, 363, 364
See application file for complete search history.

(56) References Cited

U.S. PATENT DOCUMENTS 4,588,402 A * 5/1986 Igari et al. ...................... 604/408
4,610,665 A * 9/1986 Matsumoto et al. ...... 604/167.04
(Continued)

FOREIGN PATENT DOCUMENTS

JP    4-073069 A    3/1992
JP    9-225037 A    9/1997
(Continued)

OTHER PUBLICATIONS

International Search Report (PCT/ISA/210) issued on Mar. 2, 2010, by Japanese Patent Office as the International Searching Authority for International Application No. PCT/JP2010/050775.

*Primary Examiner* — Bhisma Mehta
*Assistant Examiner* — Larry R Wilson
(74) *Attorney, Agent, or Firm* — Buchanan Ingersoll & Rooney PC (57) ABSTRACT

An elongate member housing tool assembly includes a distal end side tubular member disposed on the distal end side and a proximal end side tubular member disposed on the proximal end side, which accommodate an elongate member, and a liquid inlet port to which a liquid supplying tool for supplying liquid into the distal end side tubular member is removably connected and which is provided on the distal end side tubular member. The distal end side tubular member and the proximal end side tubular member are wound spirally, and the proximal end of the distal end side tubular member and the distal end of the proximal end side tubular member are disposed in a spaced relationship from each other. A distal portion of the guide wire is accommodated in the distal end side tubular member, except possibly the most distal portion of the elongate member.

25 Claims, 3 Drawing Sheets

(56) References Cited

U.S. PATENT DOCUMENTS

| | | | |
|---|---|---|---|
| 5,924,998 A * | 7/1999 | Cornelius et al. | 600/585 |
| 7,334,678 B2 * | 2/2008 | Kesler et al. | 206/364 |
| 8,167,902 B2 * | 5/2012 | Quinn et al. | 606/200 |
| 2007/0106260 A1 * | 5/2007 | Ishii | 604/523 |

FOREIGN PATENT DOCUMENTS

| | | |
|---|---|---|
| JP | 2004-008653 A | 1/2004 |
| JP | 2006-346075 A | 12/2006 |
| JP | 2008-093339 A | 4/2008 |

* cited by examiner

MEDICAL ELONGATE MEMBER HOUSING TOOL AND MEDICAL ELONGATE MEMBER HOUSING TOOL ASSEMBLY

This application is a continuation of International Application No. PCT/JP2010/050775 filed on Jan. 22, 2010, and claims priority to Japanese Application No. 2009-023098 filed on Feb. 3, 2009, the entire content of both of which is incorporated herein by reference.

TECHNICAL FIELD

The present invention relates to a medical elongate member housing tool and a medical elongate member housing tool assembly.

BACKGROUND DISCUSSION

A medical elongate member housing tool (e.g., a guide wire housing tool) for accommodating a medical elongate member (e.g., guide wire) is known. A known guide wire housing tool includes one tubular member wound spirally such that a proximal portion thereof is placed on the inner periphery side and a distal portion thereof is placed on the outer periphery side, and the guide wire is accommodated in the tubular member. An example of this is described in Japanese Patent Application Publication No. 2006-346075.

When the guide wire is to be used, liquid such as, for example, a physiological salt solution is first supplied from the proximal portion of the tubular member of the guide wire housing tool into the tubular member. Consequently, the liquid contacts a portion of the distal portion of the guide wire, which has a hydrophilic property, and a lubricating property is exhibited. Then, the guide wire is taken out from the guide wire housing tool. At this time, the distal portion of the guide wire is grasped by the user's fingers to pull out the guide wire from the distal portion of the tubular member.

However, in such a known guide wire housing tool, in order to cause liquid to contact the portion of the distal portion of the guide wire which has a hydrophilic property to exhibit the lubrication property, since the liquid is supplied from the proximal portion of the tubular member, it is necessary to fill the liquid into substantially the entire tubular member. Therefore, for example, in the case of a guide wire having a length of 400 cm, since the amount of the liquid to be used is great, if a small-capacity syringe which is used frequently in the medical care site is used, the liquid must be injected using many syringes and numbers of injections so that significant labor and time are required.

Further, when the guide wire is to be taken out from the guide wire housing tool, since the distal portion of the guide wire is grasped by fingers of a hand to pull out the guide wire, there is a drawback that the fingers of a hand contact a portion of the distal portion of the guide wire (portion at which a lubricating property is exhibited).

SUMMARY

A medical elongate member housing tool and a medical elongate member housing tool assembly are configured so that when liquid contacts a portion of a distal portion of a medical elongate member which has a hydrophilic property, the amount of liquid to be used can be made to a comparatively small amount and the medical elongate member can be taken out readily and rather quickly without touching the portion having the hydrophilic property.

A medical elongate member housing tool assembly includes: a medical elongate member having a distal portion and a main body portion, with the main body portion being located proximally of the distal portion, the outer surface of at least a part of the distal portion of the medical elongate member being a hydrophilic coating, and the outer surface of at least a part of the main body portion being a hydrophobic coating; a distal end side tubular member and a proximal end side tubular member, with the medical elongate member positioned inside the distal end side tubular member and the proximal end side tubular member, and the proximal end side tubular member located proximally of the distal end side tubular member, and with the distal end side tubular member having a proximal-most end and the proximal end side tubular member having a distal-most end, and with the proximal-most end of the distal end side tubular member and the distal-most end of the proximal end side tubular member being spaced apart from one another so that a portion of the medical elongate member is exposed; a liquid inlet port connected to the distal end side tubular member and in communication with an inside of the distal end side tubular member, wherein the liquid inlet port is removably connectable to a liquid supplying tool for supplying liquid into the distal end side tubular member, the distal end side tubular member and the proximal end side tubular member being wound annularly, the distal end side tubular member having a length less than the length of the proximal end side tubular member; at least a portion of the hydrophilic coating forming the outer surface of the medical elongate member which has the hydrophilic coating being accommodated in and covered by the distal end side tubular member; and the liquid inlet port being positioned proximally of the portion of the medical elongate member which has the hydrophilic coating.

Consequently, when liquid is brought into contact with the portion of the distal portion of the medical elongate member which has a hydrophilic property so as to exhibit a lubricating property, the amount of the liquid to be used can be comparatively reduced. Further, the resistance when the liquid is supplied from the liquid supplying tool can be made comparatively low, and besides, the liquid can be contacted readily with the portion which has a hydrophilic property. In other words, the liquid can be contacted economically, readily and rapidly with the portion having a hydrophilic property.

When the medical elongate member is to be taken out from the medical elongate member housing tool, the exposed portion of the medical elongate member between the proximal end of the distal end side tubular member and the distal end of the proximal end side tubular member can be grasped by fingers of a hand to feed the medical elongate member in a direction toward the distal end. Consequently, the medical elongate member can be taken out rather readily and rapidly without touching with the portion of the distal portion of the medical elongate member which has a hydrophilic property.

Preferably, the distal end side tubular member and the proximal end side tubular member satisfy the relationship b/a is equal to or greater than 3, where a is the length of the distal end side tubular member and b is the length of the proximal end side tubular member.

It is thus possible to reduce the amount of the liquid to be used when the liquid is supplied into the distal end side tubular member so as to be brought into contact with the portion of the distal portion of the medical elongate member which has a hydrophilic property thereby to exhibit a lubricating property.

The distal end side tubular member and the proximal end side tubular member are preferably wound spirally such that the proximal portion is placed on the inner periphery side while the distal portion is placed on the outer periphery side, and the liquid inlet port is positioned on the most outer periphery. Also, the distal end side tubular member and the proximal end side tubular member are preferably wound spirally such that the proximal portion is on the inner periphery side while the distal portion is on the outer periphery side, and the length of the distal end side tubular member is shorter than that of one circumference.

When connecting a liquid supplying tool to the liquid inlet port and supplying the liquid into the distal end side tubular member from the liquid supplying tool to cause the liquid to contact with the portion of the distal portion of the medical elongate member which has a hydrophilic property so as to exhibit a lubrication property, the distal end side tubular member and the proximal end side tubular member do not present an obstacle, and the operation can be carried out relatively easily and quickly.

Preferably, the liquid inlet port includes an inlet port main body portion provided halfway or at the proximal portion of the distal end side tubular member, and a tubular connection portion provided on the inlet port main body portion and having, on a side face thereof, a groove into which the medical elongate member is to be inserted, the liquid supplying tool being removably connected to the connection portion.

Consequently, the liquid supplying tool can be connected to the connection portion with certainty, and the medical elongate member can be prevented from being damaged or broken thereupon.

The connection portion is removable from the inlet port main body portion, and is configured such that, where the connection portion is attached to the inlet port main body portion, movement of the medical elongate member is blocked by the connection portion.

Consequently, the positional relationship between the medical elongate member and the medical elongate member housing tool can be fixed readily.

The medical elongate member housing tool can be configured such that attachment of the connection portion to the inlet port main body portion is carried out by fitting the connection portion into the inlet port main body portion, and by fitting the connection portion into the inlet port main body portion, the medical elongate member inserted in the groove is sandwiched by the inlet port main body portion and the connection portion thereby to block the movement of the medical elongate member.

The positional relationship between the medical elongate member and the medical elongate member housing tool can thus be fixed rather readily.

The liquid inlet port can have a first port in which the medical elongate member is disposed, and a second port to which the liquid supplying tool is removably connected.

It is thus possible to connect the liquid supplying tool to the liquid inlet port with certainty and to prevent the medical elongate member from being damaged or broken thereupon.

A valve body is provided in the inside of the first port so that leakage of the liquid from the first port can be prevented.

The liquid inlet port preferably projects in a direction of a tangential line to the distal end side tubular member wound annularly. And the injection direction of the liquid into the liquid inlet port is directed toward the distal end side.

The operation of connecting a liquid supplying tool to the liquid inlet port and supplying the liquid into the distal end side tubular member from the liquid supplying tool to cause the liquid to contact with the portion of the distal portion of the medical elongate member which has a hydrophilic property so as to exhibit a lubrication property can be carried out relatively easily and quickly.

The distal end side tubular member has, at the distal portion thereof, an inserter having a distal portion having an inner diameter and an outer diameter smaller than an inner diameter and an outer diameter of a proximal portion thereof. Consequently, for example, when the medical elongate member is to be inserted into a catheter, the medical elongate member can be inserted readily into the catheter.

The medical elongate member is configured in such a manner as to be exposed between the proximal end of the distal end side tubular member and the distal end of the proximal end side tubular member such that, when the medical elongate member is to be taken out from the medical elongate member housing tool, the exposed portion of the medical elongate member is gripped to feed the medical elongate member in a direction toward the distal end. Consequently, the medical elongate member can be taken out readily and rapidly without touching with the portion of the distal portion of the medical elongate member which has a hydrophilic property.

According to another aspect, a medical elongate member housing tool assembly includes: a medical elongate member having a distal portion and a main body portion, with the distal portion located distally of the main body portion; and a distal end side tubular member having a lumen and a proximal end side tubular member having a lumen, with the medical elongate member being positioned in the lumen of the distal end side tubular member and in the lumen of the proximal end side tubular member, the proximal end side tubular member being located proximally of the distal end side tubular member, the distal end side tubular member having a proximal-most end and the proximal end side tubular member having a distal-most end, and the proximal-most end of the distal end side tubular member and the distal-most end of the proximal end side tubular member being spaced apart from one another so that a portion of the elongate member is exposed between the proximal-most end of the distal end side tubular member and the distal-most end of the proximal end side tubular member. A liquid inlet port is connected to the distal end side tubular member and in communication with the lumen of the distal end side tubular member, the liquid inlet port being removably connectable to a liquid supplying tool for supplying liquid to the lumen of the distal end side tubular member; the distal end side tubular member has a length less than the length of the proximal end side tubular member; at least a part of the outer surface of the distal portion of the medical elongate member located distally of the liquid inlet port being a hydrophilic surface located inside the distal end side tubular member so that the liquid supplied to the lumen of the distal end side tubular member contacts the hydrophilic surface so that the hydrophilic surface exhibits lubricating properties; and the outer surface of the main body portion of the medical elongate member not being a hydrophilic surface.

Another aspect of the disclosure here involves a method of using a medical elongate member housing tool assembly that includes connecting a syringe to a liquid inlet port. The liquid inlet port is connected to a lumen in a distal end side tubular member which covers a distal portion of a medical elongate member, the distal end side tubular member possesses a distal end, the distal portion of the medical elongate member possesses a hydrophilic outer surface, and the medical elongate member includes a main body portion positioned proximally of the distal portion. A proximal end side tubular member covers at least a part of the main body portion, wherein the part of the main body portion covered by the proximal end side tubular member is devoid of the hydrophilic outer surface, and the proximal end side tubular member is located proximally of the distal end side tubular member, with the distal end side tubular member having a proximal-most end and the proximal end side tubular member having a distal-most end. The proximal-most end of the distal end side tubular member and the distal-most end of the proximal end side tubular member are spaced apart from one another so that a portion of the medical elongate member is exposed, and the distal end side tubular member has a length less than the length of the proximal end side tubular member. The method further includes supplying liquid in the syringe to the lumen in the distal end side tubular member by way of the liquid inlet port so the liquid flows toward the distal end of the distal end side tubular member and leaves the distal end side tubular member by way of the distal end, the liquid contacting and wetting the hydrophilic outer surface so that the hydrophilic outer surface exhibits lubricating properties.

DETAILED DESCRIPTION

The detailed description which follows describes features and aspects of embodiments of a medical elongate member housing tool and a medical elongate member housing tool assembly which are disclosed by way of example. The embodiments described are representative examples discussed in the context of a guide wire in which the medical elongate member is in the form of a guide wire and the medical elongate member housing tool is a guide wire housing tool and the medical elongate member housing tool assembly is a guide wire housing tool assembly.

Figure 1:
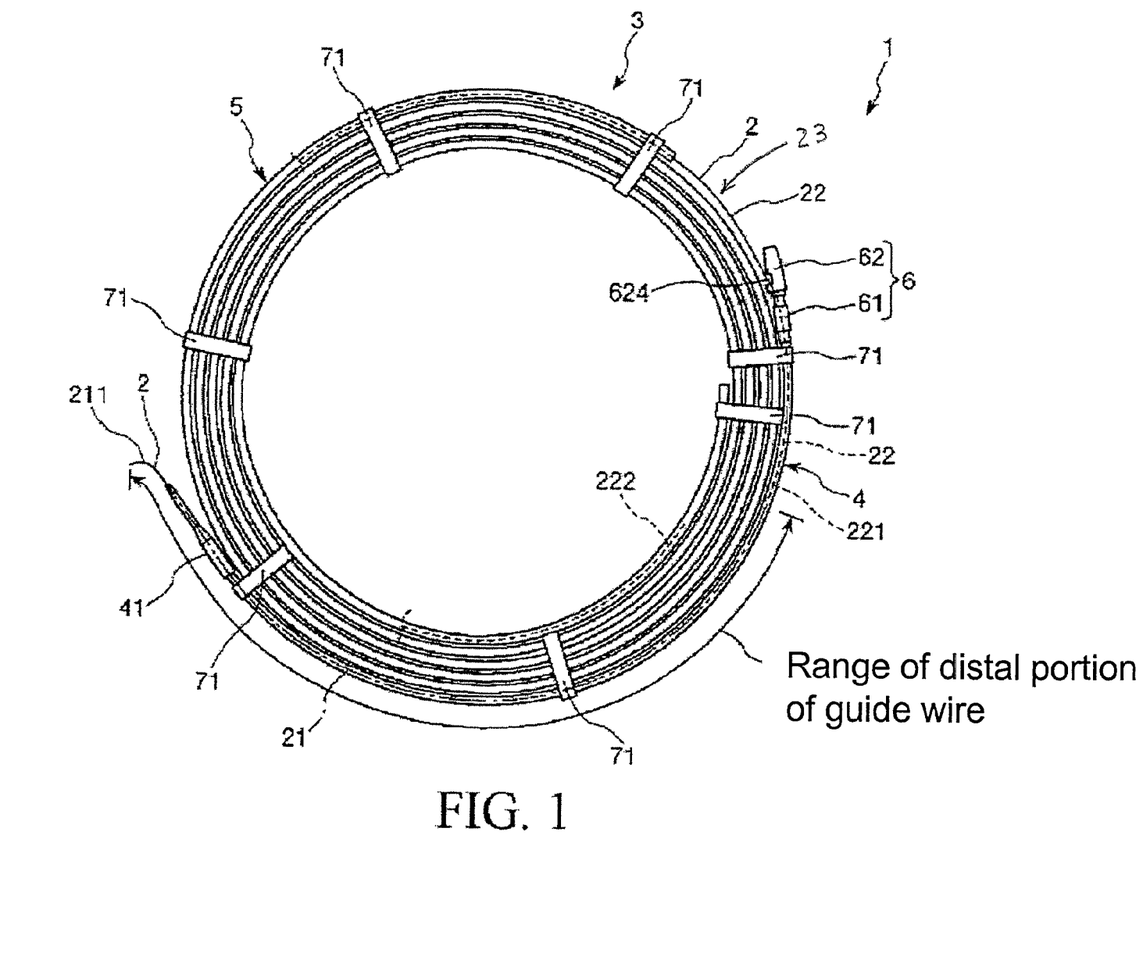
FIG. 1 is a side elevational view of a first embodiment of a medical elongate member housing tool assembly disclosed here, wherein the medical elongate member housing tool assembly is a guide wire housing tool assembly.
Figure 2:
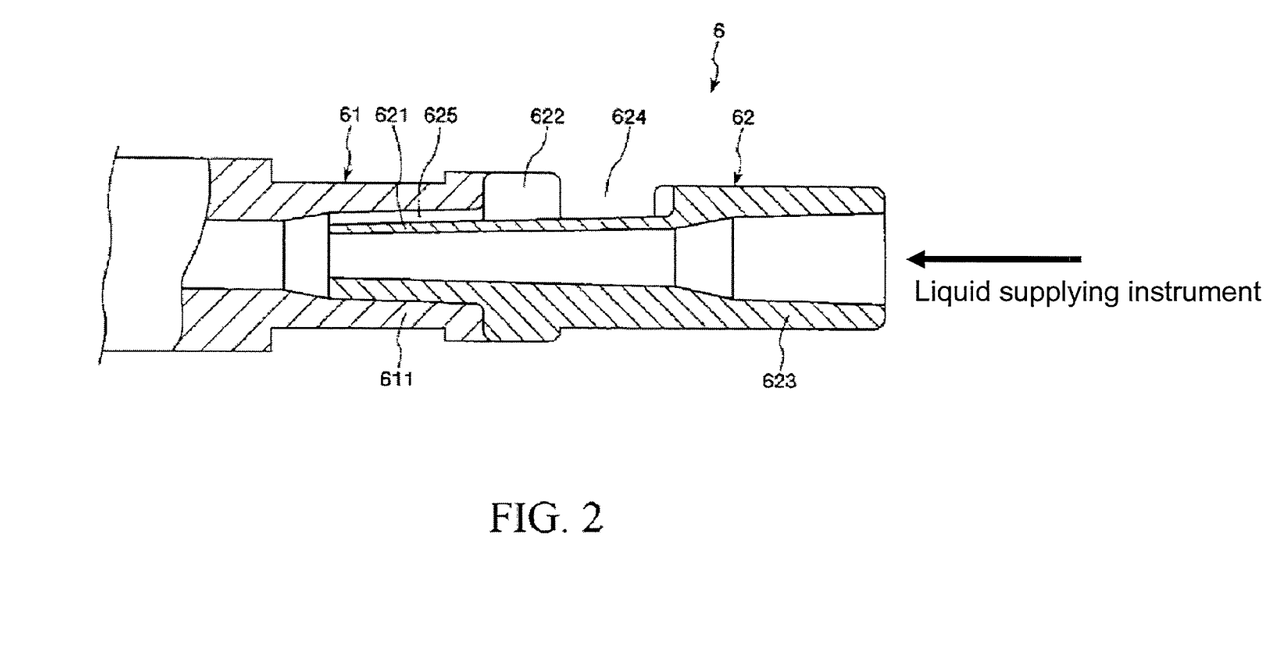
FIG. 2 is a cross-sectional view of the liquid inlet port of the guide wire housing tool assembly shown in FIG. 1.

In the following description, the clockwise direction in FIG. 1 is represented as the "distal end," the counterclockwise direction is represented as the "proximal end (rear end)," the left side in FIG. 2 is represented as the "distal end," the right side is represented as the "proximal end (rear end)," the upper side is represented as the "upper" and the lower side is represented as the "lower."

As shown in FIG. 1, a guide wire housing tool assembly (medical elongate member housing tool assembly) 1 includes a guide wire (medical elongate member) 2 and a guide wire housing tool 3 for accommodating (housing) the guide wire 2 therein.

First, the guide wire 2 to be accommodated into the guide wire housing tool 3 is described.

The guide wire 2 includes a distal portion 21 and a main body portion 22, wherein the main body portion is provided on the proximal side of the distal portion 21. In the configuration shown in FIG. 1, the guide wire 2 is configured from the distal portion 21 and the main body portion 22, with the main body portion 22 occupying most of (the majority of) the guide wire 2. In FIG. 1, to facilitate distinction between the distal portion 21 and the main body portion 22, regarding a portion of the guide wire 2 inserted (positioned) in a distal end side tubular member 4 or a proximal end side tubular member 5 hereinafter described of the guide wire housing tool 3, the distal portion 21 is indicated by an alternate long and short dash line while the main body portion 22 is indicated by a broken line. More specifically, FIG. 1 illustrates the range or extent of the distal portion 21 of the guide wire. The distal end portion 221 of the main body portion of the guide wire is connected to and extends from the proximal end of the distal portion 21 of the guide wire 2. The main body portion 22 of the guide wire 2 extends from the distal end portion 221 to the proximal end portion 222.

This guide wire 2 includes a portion (hydrophilic portion) in which a hydrophilic property is exhibited on the surface of the distal portion 21 and also includes another portion (hydrophobic portion) in which a hydrophobic property is exhibited on the surface of the main body portion 22. The portion having the hydrophilic property is a portion at which a lubricating property is exhibited by contact with liquid. The structure of the guide wire, the material forming the guide wire and so forth are not limited specifically so long as a material is used with which a hydrophilic portion and a hydrophobic portion are provided on the surface of the distal portion 21 and the surface of the main body portion 22, respectively. A preferable material or construction involves a core configured, for example, from a super elastic metal wire while the outer surface of the core is covered with a coating layer made of resin hereinafter described.

While the material forming the core is not specifically limited, a super elastic alloy or the like such as a Ni—Ti-based alloy is one preferable example.

Further, while the outer diameter (diameter) of the guide wire 2 is not specifically limited, it is preferable to use a guide wire possessing an outer diameter of 1.0 mm or less, more preferably approximately 0.3 mm to 0.9 mm.

A most distal portion 211 of the distal portion 21 of the guide wire 2 has a curved shape, for example, a J-shape in a natural state in which no external force is applied, and, upon application of an external force is applied, then the most distal portion 211 is elastically deformed to a different shape (for example, a linear shape), but, if the application of the external force is removed, then the most distal portion 211 returns or is restored to its original shape by a restoring force. The shape of the most distal portion 211 of the guide wire 2 is not limited to the shape described above, and the most distal portion 211 may not be curved, for example, in a natural state in which no external force is applied.

Further, as described hereinabove, a hydrophobic material such as, for example, fluorine-based resin (PTFE, ETFE, PFA or the like) is coated on or applied to the outer surface of the main body portion 22 of the guide wire 2. In other words, a coating layer having a hydrophobic property exists as the outermost surface of the main body portion 21 of the guide wire 2.

A hydrophilic material is coated on or applied to the outer surface of the distal portion 21 of the guide wire 2. In other words, a coating layer having a hydrophilic property exists as the outermost surface of the distal portion 21 of the guide wire 2. If the hydrophilic material is wetted, the surface develops or exhibits a lubricating property, and the friction (sliding resistance) of the outer surface of the distal portion 21 of the guide wire 2 decreases and the sliding property of the guide wire 2 in a body cavity such as a blood vessel or an appliance such as a catheter is enhanced. Accordingly, the operability upon operation of the guide wire 2 such as advancing or retreating movement, or rotation is enhanced.

The hydrophilic material includes, for example, polymeric substances derived from cellulose, polymeric substances derived from polyethylene oxide, polymeric substances derived from maleic anhydride (such as maleic anhydride copolymer composed of methyl vinyl ether and maleic anhydride), polymeric substances derived from acrylamide (such as polyacrylamide and block copolymer of polyglycidyl methacrylate (PGMA) and dimethylacrylamide (DMAA)), water-soluble nylon, polyvinyl alcohol, and polyvinyl pyrrolidone.

In most cases, such a hydrophilic material as described above exhibits a lubricating property when it is wetted and decreases the friction resistance (sliding resistance) between a body cavity such as a blood vessel into which the guide wire 2 is inserted and an inner wall face (inner surface) of the appliance. Consequently, the sliding property of the guide wire 2 is enhanced and the operability of the guide wire 2 becomes still better.

Now, the guide wire housing tool 3 is described. The guide wire housing tool 3 includes a distal end side tubular member 4 disposed on the distal end side and a proximal end side tubular member 5 disposed on the proximal end side, which accommodate the guide wire 2 therein, and a liquid inlet port 6 to which a liquid supplying tool (for example, a syringe or the like) for supplying liquid into the distal end side tubular member 4 is removably connected. The liquid inlet port 6 is disposed at the proximal portion of the distal end side tubular member 4. The inside of the distal end side tubular member 4 and the proximal end side tubular member 5 are each configured as an accommodation section for accommodating the guide wire 2 therein.

The distal end side tubular member 4 has a hard inserter 41 at the distal portion thereof. In particular, the distal end side tubular member 4 has a main body and the inserter 41 provided at the distal end of the main body.

The inserter 41 has a tapering shape. In particular, the inner diameter and the outer diameter of the distal portion of the inserter 41 are smaller than the inner diameter and the outer diameter of the proximal portion of the inserter 41, respectively. The inner and outer diameters of the inserter 41 thus taper in a narrowing manner from the proximal end toward the distal end. The inserter 41 may be removably provided on, or fixedly attached to, the main body of the distal end side tubular member 4.

When the guide wire 2 is to be inserted, for example, into a catheter or the like, before insertion of the guide wire 2, the inserter 41 is connected to a hub of the catheter. Since the most distal portion 211 of the guide wire 2 is curved in a j shape, the guide wire 2 can be relatively easily inserted into the catheter by the inserter 41.

The main body of the distal end side tubular member 4 and the proximal end side tubular member 5 are configured individually from a tube having flexibility, and the distal end side tubular member 4 and the proximal end side tubular member 5 are wound annularly. In particular, the distal end side tubular member 4 and the proximal end side tubular member 5 are wound spirally such that the proximal portion thereof is located on the inner periphery side (radially inner side) while the distal portion thereof is located on the outer periphery side (radially outer side). Each of the distal end side tubular member 4 and the proximal end side tubular member 5 wound spirally is hereinafter referred to sometimes as "spiral body". The proximal-most end of the distal end side tubular member 4 and the distal-most end of the proximal end side tubular member 5 are disposed in a spaced relationship from each other.

Further, the shape (state) of the distal end side tubular member 4 and the proximal end side tubular member 5 is retained by a plurality of retaining members 71. In the illustrated embodiment, the retaining members 71 are in the form of clips (seven in the configuration shown in FIG. 1) each having a plurality of (five in the configuration shown in FIG. 1) through-holes in a state in which they are wound spirally, that is, in a bundled state.

The most distal portion 211 of the guide wire 2 is exposed from the distal end of the distal end side tubular member 4 and further from the distal end of the inserter 41, to the outside and is stored in a state in which the main body proximal portion 222 which is a proximal portion of the main body 22 is inserted in the proximal end side tubular member 5 until it is used. By exposing the most distal portion 211 of the guide wire 2 to the outside, the shape of the most distal portion 211 can be inhibited or prevented from being deformed to a somewhat elongated shape similar to a situation in which the most distal portion 211 is inserted or positioned for a long period of time in the distal end side tubular member 4.

The distal portion 21 of the guide wire 2 which is a portion having a hydrophilic property is accommodated in the distal end side tubular member 4 except for the most distal portion 211. In a state in which the most distal portion 211 is accommodated in the distal end side tubular member 4, the distal portion 21 which is a portion having the hydrophilic property is entirely accommodated in the distal end side tubular member 4.

Further, an intermediate portion of the main body portion 22, which is a portion of the guide wire 2 having a hydrophobic property, is positioned between the proximal-most end of the distal end side tubular member 4 and the distal-most end of the proximal end side tubular member 5 and is exposed to the outside. This exposed intermediate portion 23 of the main body portion 22 of the guide wire that is exposed between the proximal-most end of the distal end side tubular member 4 and the distal-most end of the proximal end side tubular member 5 is grasped by fingers of the user's hand and an operation for feeding the guide wire 2 to a distal end direction or a proximal end direction is carried out.

The proximal-most end of the distal end side tubular member 4 and the distal-most end of the proximal end side tubular member 5 are spaced away from each other by a length (distance) which allows the exposed main body portion 22 to be grasped by fingers of a user's hand and the guide wire 2 can be fed in the distal end direction or the proximal end direction.

While the spaced distance (gap distance) between the proximal-most end of the distal end side tubular member 4 and the distal-most end of the proximal end side tubular member 5 is not limited to a specific distance, it is preferable to set the distance to approximately 3 to 20 cm, more preferably approximately 5 to 15 cm. Consequently, the operation for feeding the guide wire 2 can be relatively easily carried out.

Further, the length of the distal end side tubular member 4 is shorter than the length of the proximal end side tubular member 5. In particular, where the length of the distal end side tubular member 4 is represented by a and the length of the proximal end side tubular member 5 is represented by b, it is preferable to set b/a to 3 or greater, more preferably 4 or greater, and still more preferably approximately 5 to 11. Consequently, the amount of liquid to be used can be decreased when liquid is supplied into the distal end side tubular member 4 to cause the liquid to contact the hydrophilic coating layer of the distal portion 21 of the guide wire 2 to thereby exhibit a lubricating property.

Further, the length of the distal end side tubular member 4 is shorter than the length of one circumference of the spiral body (the distal end side tubular member 4 does not make one full circumference). The liquid inlet port 6 is thus positioned on the outer-most periphery of the spiral body. Consequently, in the operation of connecting the liquid supplying tool to the liquid inlet port 6 and supplying the liquid into the distal end side tubular member 4 from the liquid supplying tool to cause the liquid to contact with the hydrophilic coating layer of the distal portion 21 of the guide wire 2 to exhibit a lubrication property (the operation is hereinafter referred to simply as "liquid supplying operation"), the distal end side tubular member 4 and the proximal end side tubular member 5 do not present an obstacle to the operation, and the operation can be carried out relatively easily and quickly.

Further, by limiting the position of the liquid inlet port 6 to the proximal portion of the distal end side tubular member 4, the operator (operating person) can supply the liquid without mistaking the liquid inlet port 6.

The size and the number of windings (winding amount) of the spiral body, that is, of the distal end side tubular member 4 and the proximal end side tubular member 5, is not limited to a particular amount, but is suitably set in accordance with various conditions such as the length of the guide wire 2. The number of windings of the spiral body is preferably approximately 3 to 10, more preferably approximately 4 to 6.

Further, while the material forming the distal end side tubular member 4 and the proximal end side tubular member 5 is not limited, examples of suitable materials include various resin materials or the like. The distal end side tubular member 4 and the proximal end side tubular member 5 may be individually configured, for example, from a hard material such as hard resin, metal or the like. Further, the distal end side tubular member 4 and the proximal end side tubular member 5 may be individually configured such that the inside thereof can be visually observed.

As shown in FIG. 2, the liquid inlet port 6 includes a tubular inlet port main body portion 61 fixed to the proximal portion of the distal end side tubular member 4 and a tubular connection portion 62 to which a liquid supplying tool not shown is removably connected.

The connection portion 62 is removably connected to the inlet port main body portion 61. Mounting of the connection portion 62 on the inlet port main body portion 61 is carried out by fitting the connection portion 62 into the inlet port main body portion 61.

The distal portion 621 of the connection portion 62 is a portion configured to be fitted into a proximal portion 611 of the inlet port main body portion 61, and an enlarged diameter portion 622 is formed on the proximal end side of the distal portion 621. The enlarged diameter portion 622 abuts the proximal end of the inlet port main body portion 61 when the distal portion 621 of the connection portion 62 is fitted into the proximal portion 611 of the inlet port main body portion 61.

A proximal portion 623 of the connection portion 62 is a portion to which a liquid supplying tool is to be connected.

The connection portion 62 has a cutaway portion 624 on a side face of the outer periphery side between the enlarged diameter portion 622 and the proximal portion 623.

The connection portion 62 has a groove 625 on a side face thereof on the outer periphery side. The groove 625 extends from the distal end of the connection portion 62 to the enlarged diameter portion 622 and is communicated with the cutaway portion 624, and the guide wire 2 is inserted into the groove 625. In particular, in a state in which the connection portion 62 is attached to the inlet port main body portion 61, the guide wire 2 is inserted in the groove 625 and is exposed to the outside from the cutaway portion 62 through the groove 625. Consequently, the liquid supplying tool can be connected with certainty to the proximal portion 623 of the connection portion 62 and the guide wire 2 can be prevented from being damaged or broken.

Further, the liquid inlet port 6 is configured such that, when the connection portion 62 is attached to the inlet port main body portion 61, movement of the guide wire 2 is blocked by the connection portion 62. In particular, if the connection portion 62 is fitted into the inlet port main body portion 61, then the guide wire 2 inserted in the groove 625 is sandwiched by the inlet port main body portion 61 and the connection portion 62 thereby to block movement of the guide wire 2. Consequently, the positional relationship between the guide wire 2 and the guide wire housing tool 3 is fixed.

This liquid inlet port 6 projects in a direction of a tangential line to the proximal portion of the distal end side tubular member 4 as shown in FIG. 1. Then, the injection direction of liquid into the liquid inlet port 6 is directed to the distal end side. Consequently, a liquid supplying operation can be carried out readily and rapidly.

Although the material forming each of the inlet port main body portion 61 and the connection portion 62 is not particularly limited, various resin materials, metal materials and so forth can be used by way of example. Further, the inlet port main body portion 61 and the connection portion 62 may be configured such that the inside thereof can be visually observed.

Now, an example of operation of the guide wire housing tool assembly 1 (guide wire housing tool 3), that is a procedure in which the guide wire 2 accommodated in the guide wire housing tool 3 is used, is described with reference to FIG. 1.

A syringe (liquid supplying tool) containing liquid such as, for example, physiological salt solution is connected to the connection portion 62 of the liquid inlet port 6, and the liquid is supplied from the syringe into the distal end side tubular member 4. The supplied liquid flows in a direction toward the distal end in the distal end side tubular member 4, and consequently, the liquid is contacted with the outer surface of the distal portion 21 of the guide wire 2, that is, the hydrophilic coating layer, and a lubricating property is exhibited. Also the most distal portion 211 of the guide wire 2 exposed from the distal end of the inserter 41 is wetted at its outer surface to thereby exhibit a lubricating property as the liquid blows out from the end of the inserter 41 or the liquid goes along the most distal portion 211.

Then, the guide wire 2 is taken out from the guide wire housing tool 3. But first, the connection portion 62 is removed from the inlet port main body portion 61 so that movement of the guide wire 2 is permitted.

To remove the guide wire 2 from the guide wire housing tool 3, the main body portion 22 of the guide wire 2 exposed between the proximal end of the distal end side tubular member 4 and the distal end of the proximal end side tubular member 5 (i.e., the exposed portion 23) is grasped by fingers of a user's hand, and the guide wire 2 is moved in a direction toward the distal end. Consequently, the guide wire 2 is gradually pushed out from the distal end (distal end side) of the distal end side tubular member 4 to the outside. Since the surface of the main body portion 22 has a hydrophobic property, the fingers of the user's hand are less likely to slip on the surface of the main body portion 22 than on the portion which has a hydrophilic property and can be grasped readily, and even if the guide wire is 400 cm long and is comparatively long, it can be moved readily.

Then, after a main body distal portion 221, which is a distal portion of the main body portion 22 of the guide wire 2, is pushed out from the distal end (distal end side) of the distal end side tubular member 4 to the outside, the main body distal portion 221 is grasped by fingers of a user's hand and the guide wire 2 is pulled out from the distal end of the distal end side tubular member 4.

In this manner, the guide wire 2 can be taken out readily and rapidly without touching the hydrophilic coating layer of the distal portion 21 of the guide wire 2.

As described above, with this guide wire housing tool 3 (guide wire housing tool assembly 1), since the liquid inlet port 6 is provided at the proximal portion of the distal end side tubular member 4, when liquid is contacted with the hydrophilic coating layer of the distal portion 21 of the guide wire 2 to cause the hydrophilic coating layer to exhibit a lubricating property, the amount of liquid to be used can be reduced to a comparatively small amount and the resistance when liquid is supplied from the liquid supplying tool can be made comparatively low while the liquid can be contacted rapidly with the hydrophilic coating layer. That is, liquid can be contacted economically, readily and rapidly with the hydrophilic coating layer.

Also, because the distal end side tubular member 4 has the inserter 41 provided at the distal portion thereof, flowing out of liquid supplied into the distal end side tubular member 4 can be suppressed by the inserter 41, and the residence time of the liquid in the distal end side tubular member 4, particularly on the distal end side of the distal end side tubular member 4, can be made comparatively long. Consequently, lubricating characteristics can be provided with certainty to the hydrophilic coating layer of the guide wire 2.

Because the direction in which the liquid flows and the direction in which the guide wire 2 is moved when the guide wire 2 is to be taken out from the guide wire housing tool 3 are same as each other, the direction in which the guide wire 2 is to be moved can be known readily, and even an operator (operating person) who is not skilled can take out the guide wire 2 readily, rapidly and with certainty.

As mentioned, the proximal end of the distal end side tubular member 4 and the distal end of the proximal end side tubular member 5 are disposed in a spaced relationship from each other. When the guide wire 2 is to be taken out from the guide wire housing tool 3, the main body portion 22 of the guide wire 2 exposed between the proximal end of the distal end side tubular member 4 and the distal end of the proximal end side tubular member 5 can be grasped by fingers of a user's hand to feed the guide wire 2 in a direction toward the distal end. Consequently, the guide wire 2 can be taken out rather readily and rapidly without touching the hydrophilic coating layer of the distal portion of the guide wire 2.

Different from this guide wire housing tool 3, in a housing tool wherein a liquid instruction port is provided at a distal portion of a distal end side tubular member, if the guide wire 2 is positioned at a place of the liquid introduction port, a liquid supplying tool cannot be connected to the liquid introduction port or, even if a liquid supplying tool can be connected, the guide wire 2 is sometimes damaged or broken. However, with this guide wire housing tool 3, since the liquid inlet port 6 is provided at the proximal portion of the distal end side tubular member 4, it is possible to connect a liquid supplying tool with certainty to the liquid inlet port 6 and prevent the guide wire 2 from being damaged or broken.

In the assembly disclosed here, a duckbill valve or the like may be provided at the distal portion of the distal end side tubular member 4. In this instance, the direction of the duckbill valve is set such that the guide wire 2 can moved readily in the direction toward the distal end. Consequently, flowing out of liquid from the distal end of the distal end side tubular member 4 can be prevented (or suppressed), and consequently, the amount of liquid to be used can be further reduced.

Figure 3:
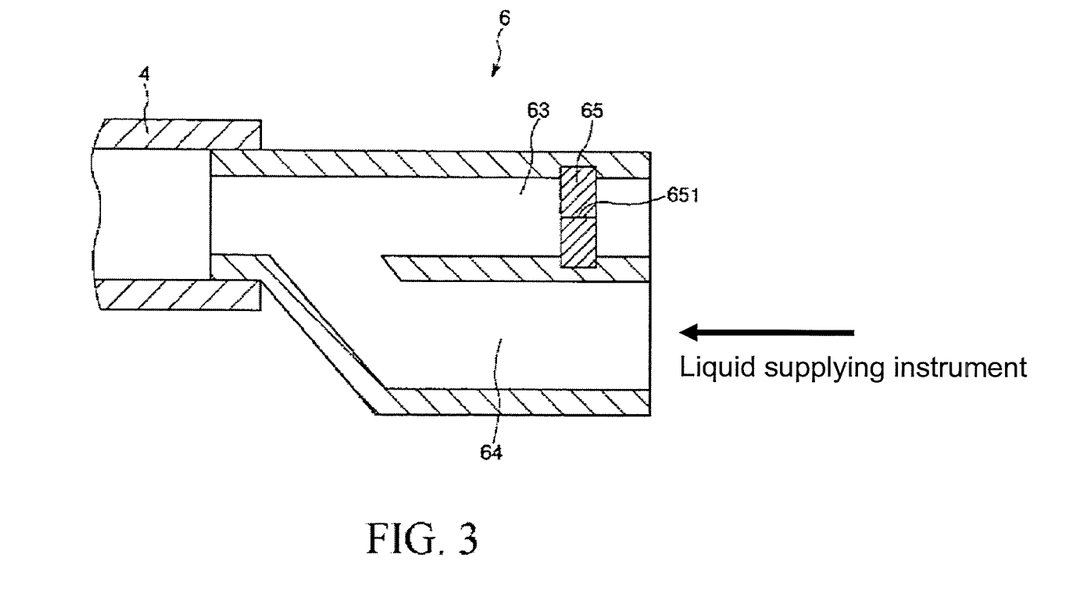
FIG. 3 is a cross-sectional view showing a liquid inlet port in a second embodiment where the medical elongate member housing tool assembly of the present invention is applied to a guide wire housing tool assembly.

FIG. 3 is a cross-sectional view of a liquid inlet port in a second embodiment in the case where the medical elongate member housing tool assembly is applied to a guide wire housing tool assembly. In the following description, the left side in FIG. 3 is represented as the "distal end," the right side is represented as the "proximal end (rear end)," the upper side is represented as the "upper" and the lower side is represented as the "lower."

The following description of the second embodiment focuses primarily on the differences relative to the first embodiment described above. Thus, features associated with this second embodiment that are the same as in the first embodiment are not described again in detail.

The second embodiment is similar to the first embodiment except that the configuration of the liquid introduction port is different.

As shown in FIG. 3, in the guide wire housing tool 3 of the guide wire housing tool assembly 1 of the second embodiment, the liquid inlet port 6 has a first port 63 in which the guide wire 2 is to be disposed, and a second port 64 to which a liquid supplying tool is removably connected, and is secured (securely provided) at a distal portion thereof to a proximal portion of the distal end side tubular member 4. The lumen of the first port 63 and the lumen of the second port 64 are joined together at distal portions thereof.

A valve body 65 is provided inside the first port 63. The valve body 65 includes a normally closed slit 651 (opening and closing port) which can be opened and closed. The normally closed slit 651 is installed such that it closes the lumen of the first port 63 while the guide wire 2 is fitted in the slit 651 of the valve body 65. Consequently, when a liquid supplying tool is connected to the second port 64 and liquid is supplied into the distal end side tubular member 4 from the liquid supplying tool, leakage of the liquid from the first port 63 can be prevented.

The guide wire housing tool assembly according to this second embodiment is similar in effects to those of the first embodiment described above.

The inner diameter of the first port 63 may be reduced, that is the gap between the guide wire 2 and the inner wall portion of the first port 63 may be made very small with the valve body 65 omitted. With this configuration just described, the guide wire 2 can be moved readily and smoothly while leakage of liquid from the first port 63 is suppressed.

While the medical elongate member housing tool and the medical elongate member housing tool assembly disclosed here are described based on the embodiments shown in the drawings, the invention is not limited to the details disclosed, and the configuration of the individual elements can be replaced by other features having similar or substantially similar functions. Further, other features may be added.

The assembly may also be a combination of two or more configurations or features of the embodiments described above.

The liquid inlet port (inlet port main body portion) may be provided halfway of the distal end side tubular member. That is, the liquid inlet port (inlet port main body portion) may be provided at an intermediate portion of the distal end side tubular member. In this instance, the portion of the medical elongate member which has a hydrophilic property is preferably accommodated in the distal end side tubular member on the distal end side with respect to the liquid introduction port.

Further, the inserter may be omitted.

The medical elongate member is not limited to a guide wire. The disclosure here is also applicable to other elongate members having a distal portion and a main body portion provided on the proximal end side of the distal portion and including a portion having a hydrophilic property on the surface of the distal portion and a portion having a hydrophobic property on the surface of the main body portion. By way of example, the medical elongate member can be a catheter.

According to the disclosure here, because a liquid introduction port is provided halfway or at a proximal portion of a distal end side tubular member, when liquid is brought into contact with a portion at the distal portion of the medical elongate member which has a hydrophilic property so that the portion may exhibit a lubricating property, the amount of the liquid to be used can be made comparatively small and the resistance when liquid is supplied from a liquid supplying tool can be made comparatively low. Further, the liquid can be brought into contact rather rapidly with the portion of the medical elongate member which has a hydrophilic property. In other words, the liquid can be brought into contact economically, readily and quickly with the portion having the hydrophilic property. Further, because the proximal end of a distal end side tubular member and the distal end of a proximal end side tubular member are disposed in a spaced relationship from each other, when the medical elongate member is to be taken out from the medical elongate member accommodating tool, an exposed portion of the medical elongate member between the proximal end of the distal end side tubular member and the distal end of the proximal end side tubular member can be grasped by fingers of a user's hand to feed the medical elongate member in a direction toward the distal end. Consequently, the medical elongate member can be taken out readily and rapidly without touching with the portion at the distal portion of the medical elongate member which has a hydrophilic property.

The detailed description above describes features and aspects of embodiments of a medical elongate member housing tool and a medical elongate member housing tool assembly disclosed by way of example. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical elongate member housing tool assembly comprising:
   a medical elongate member having a distal portion and a main body portion, the distal portion and the main body portion having an outer surface, the main body portion being located proximally of the distal portion, the outer surface of at least a part of the distal portion of the medical elongate member being a hydrophilic coating, and the outer surface of at least a part of the main body portion being a hydrophobic coating;
   a distal end side tubular member and a proximal end side tubular member, the medical elongate member being positioned inside the distal end side tubular member and the proximal end side tubular member, the proximal end side tubular member being located proximally of the distal end side tubular member, the distal end side tubular member having a proximal-most end and the proximal end side tubular member having a distal-most end, the proximal-most end of the distal end side tubular member and the distal-most end of the proximal end side tubular member being spaced apart from one another so that a portion of the medical elongate member is exposed between the proximal-most end of the distal end side tubular member and the distal-most end of the proximal end side tubular member;
   a liquid inlet port connected to the distal end side tubular member and in communication with an inside of the distal end side tubular member, the liquid inlet port being removably connectable to a liquid supplying tool for supplying liquid into the distal end side tubular member;
   the distal end side tubular member and the proximal end side tubular member being wound annularly, the distal end side tubular member having a length less than the length of the proximal end side tubular member;
   at least a portion of the hydrophilic coating forming the outer surface of the medical elongate member which has the hydrophilic coating being accommodated in and covered by the distal end side tubular member; and
   the liquid inlet port being positioned proximally of the portion of the medical elongate member which has the hydrophilic coating.

2. The medical elongate member housing tool assembly according to claim 1, wherein the proximal end side tubular member and the distal end side tubular member are configured to satisfy b/a is equal to or greater than 3, wherein a is the length of the distal end side tubular member and b is the length of the proximal end side tubular member.

3. The medical elongate member housing tool assembly according to claim 1, wherein the distal end side tubular member and the proximal end side tubular member are wound spirally to form a spiral winding such that a proximal portion of the proximal end side tubular member is on an inner periphery side while a distal portion of the distal end side tubular member is on an outer periphery side, and the liquid inlet port is positioned on an outer-most periphery of the spiral winding.

4. The medical elongate member housing tool assembly according to claim 3, wherein the length of the distal end side tubular member is less than the circumference of the spiral winding.

5. The medical elongate member housing tool assembly according to claim 1, wherein the liquid inlet port includes a tubular inlet port main body portion fixed to a proximal end portion of the distal end side tubular member and a tubular connection portion configured to be removably connected to the liquid supplying tool.

6. The medical elongate member housing tool assembly according to claim 5, wherein the tubular inlet port main body portion includes a proximal end face in contact with an enlarged diameter portion of the connection portion, and the connection portion has a cutaway portion between the enlarged diameter portion of the connection portion and a proximal portion of the connection portion.

7. The medical elongate member housing tool assembly according to claim 6, wherein the connection portion includes a groove on an outer peripheral surface of the connection portion, the groove extending from a distal-most end of the connection portion to the enlarged diameter portion and being in communication with the cutaway portion, the medical elongate member being positioned in the groove and exposed to outside the liquid inlet port.

8. The medical elongate member housing tool assembly according to claim 1, wherein the liquid inlet port includes a first port in which the medical elongate member is disposed and a second port removably connectable to the liquid supplying tool, a distal portion of the first port and a distal portion of the second port being joined together and fluidly communicating with each other.

9. The medical elongate member housing tool assembly according to claim 8, further comprising a valve body inside the first port, the valve body including an openable and closable slit through which the medical elongate member passes, the slit closing the first port while the elongate member passes through the slit.

10. The medical elongate member housing tool assembly according to claim 1, wherein the proximal end side tubular member possesses a proximal-most end that is positioned radially inwardly of the proximal-most end of the distal end side tubular member.

11. The medical elongate member housing tool assembly according to claim 1, wherein the proximal end side tubular member possesses a proximal-most end that is positioned radially inwardly of the distal-most end of the proximal end side tubular member.

12. The medical elongate member housing tool assembly according to claim 1, wherein the proximal end side tubular member possesses a proximal-most end that is positioned radially inwardly of both the distal-most end of the proximal end side tubular member and the proximal-most end of the distal end side tubular member.

13. The medical elongate member housing tool assembly according to claim 1, wherein at least a portion of the distal portion of the medical elongate member coated with the hydrophilic coating protrudes from the distal end side tubular member so that a portion of the hydrophilic coating is positioned inside the distal end side tubular member and an other portion of the hydrophilic coating is positioned exterior to the distal end side tubular member.

14. The medical elongate member housing tool assembly according to claim 1, wherein the portion of the medical elongate member possessing the hydrophobic coating is positioned at least between the proximal-most end of the distal end side tubular member and the distal-most end of the proximal end side tubular member.

15. A medical elongate member housing tool assembly comprising:
a medical elongate member possessing an outer surface, the medical elongate member having a distal portion and a main body portion, with the distal portion located distally of the main body portion;
a distal end side tubular member having a lumen and a proximal end side tubular member having a lumen, the medical elongate member being positioned in the lumen of the distal end side tubular member and in the lumen of the proximal end side tubular member, the proximal end side tubular member being located proximally of the distal end side tubular member, the distal end side tubular member having a proximal-most end and the proximal end side tubular member having a distal-most end, the proximal-most end of the distal end side tubular member and the distal-most end of the proximal end side tubular member being spaced apart from one another so that a portion of the elongate member is exposed between the proximal-most end of the distal end side tubular member and the distal-most end of the proximal end side tubular member;
a liquid inlet port connected to the distal end side tubular member and in communication with the lumen of the distal end side tubular member, the liquid inlet port being removably connectable to a liquid supplying tool for supplying liquid to the lumen of the distal end side tubular member;
the distal end side tubular member having a length less than the length of the proximal end side tubular member;
at least a part of the outer surface of the distal portion of the medical elongate member located distally of the liquid inlet port being a hydrophilic surface located inside the distal end side tubular member so that the liquid supplied to the lumen of the distal end side tubular member contacts the hydrophilic surface so that the hydrophilic surface exhibits lubricating properties; and
the outer surface of the main body portion of the medical elongate member not being a hydrophilic surface.

16. The medical elongate member housing tool assembly according to claim 15, wherein a distal end portion of the medical elongate member extends distally beyond a distal-most end of the distal end side tubular member.

17. The medical elongate member housing tool assembly according to claim 15, wherein the proximal end side tubular member and the distal end side tubular member are configured to satisfy b/a is equal to or greater than 3, wherein a is the length of the distal end side tubular member and b is the length of the proximal end side tubular member.

18. The medical elongate member housing tool assembly according to claim 15, wherein the medical elongate member is a guide wire.

19. The medical elongate member housing tool assembly according to claim 15, wherein the liquid inlet port includes a tubular inlet port main body portion fixed to a proximal end portion of the distal end side tubular member and a tubular connection portion configured to be removably connected to the liquid supplying tool.

20. The medical elongate member housing tool assembly according to claim 19, wherein the tubular inlet port main body portion includes a proximal end face in contact with an enlarged diameter portion of the connection portion, and the connection portion has a cutaway portion between the enlarged diameter portion of the connection portion and a proximal portion of the connection portion.

21. The medical elongate member housing tool assembly according to claim 20, wherein the connection portion includes a groove on an outer peripheral surface of the connection portion, the groove extending from a distal-most end of the connection portion to the enlarged diameter portion and being in communication with the cutaway portion, the medical elongate member being positioned in the groove and exposed to outside the liquid inlet port.

22. The medical elongate member housing tool assembly according to claim 15, wherein the liquid inlet port includes a first port in which the medical elongate member is disposed and a second port removably connectable to the liquid supplying tool, a distal portion of the first port and a distal portion of the second port being joined together and fluidly communicating with each other.

23. The medical elongate member housing tool assembly according to claim 22, further comprising a valve body inside the first port, the valve body including an openable and closable slit through which the medical elongate member passes, the slit closing the first port while the elongate member passes through the slit.

24. A method of using a medical elongate member housing tool assembly comprising:
connecting a syringe to a liquid inlet port, the liquid inlet port being connected to a lumen in a distal end side tubular member which covers a distal portion of a medical elongate member, the distal end side tubular member possessing a distal end, the distal portion of the medical elongate member possessing a hydrophilic outer surface, the liquid inlet port being positioned proximally of the distal portion of the medical elongate member possessing the hydrophilic outer surface, the medical elongate member also including a main body portion positioned proximally of the distal portion, and including a proximal end side tubular member covering at least a part of the main body portion, the part of the main body portion covered by the proximal end side tubular member being devoid of the hydrophilic outer surface, the proximal end side tubular member being located proximally of the distal end side tubular member, the distal end side tubular member having a proximal-most end and the proximal end side tubular member having a distal-most end, the proximal-most end of the distal end side tubular member and the distal-most end of the proximal end side tubular member being spaced apart from one another so that a portion of the medical elongate member is exposed, the distal end side tubular member having a length less than the length of the proximal end side tubular member; and supplying liquid in the syringe to the lumen in the distal end side tubular member by way of the liquid inlet port so the liquid flows toward the distal end of the distal end side tubular member and leaves the distal end side tubular member by way of the distal end, the liquid contacting and wetting the hydrophilic outer surface so that the hydrophilic outer surface exhibits lubricating properties.

25. The method according to claim 24, further comprising grasping the portion of the medical elongate member that is exposed between the proximal-most end of the distal end side tubular member and the distal-most end of the proximal end side tubular member after the hydrophilic outer surface is wetted, and moving the medical elongate member in a distal direction relative to the distal end side tubular member to push the medical elongate member out the distal end of the distal end side tubular member.

* * * * *